United States Patent [19]
Evans

[11] Patent Number: 6,083,254
[45] Date of Patent: Jul. 4, 2000

[54] REUSABLE HOT/COLD THERAPEUTIC COMPRESS APPLIANCE

[76] Inventor: Randy Allan Evans, 171 Pemberton Ave., North Vancouver, B. C., Canada, V7P 2R4

[21] Appl. No.: 08/823,067

[22] Filed: Mar. 21, 1997

Related U.S. Application Data

[60] Provisional application No. 60/013,935, Mar. 22, 1996.

[51] Int. Cl.⁷ ..................................................... A61F 7/00
[52] U.S. Cl. ........................... 607/96; 607/108; 607/112; 607/114
[58] Field of Search ............................ 126/204; 165/46; 607/104, 108–112, 114

[56] References Cited

U.S. PATENT DOCUMENTS

| | | |
|---|---|---|
| 3,822,705 | 7/1974 | Pilotte . |
| 3,871,376 | 3/1975 | Kozak . |
| 3,885,403 | 5/1975 | Spencer . |
| 3,900,035 | 8/1975 | Welch et al. ............................ 607/108 |
| 4,055,188 | 10/1977 | Pelton . |
| 4,092,982 | 6/1978 | Salem . |
| 4,204,543 | 5/1980 | Henderson . |
| 4,585,003 | 4/1986 | Meistrell ................................. 607/108 |
| 4,676,247 | 6/1987 | Van Cleve ............................... 607/108 |
| 4,756,311 | 7/1988 | Francis, Jr. . |
| 4,858,259 | 8/1989 | Simmons et al. . |
| 4,920,964 | 5/1990 | Francis, Jr. . |
| 5,129,391 | 7/1992 | Brodsky et al. . |
| 5,305,471 | 4/1994 | Steele et al. ........................ 607/108 X |

Primary Examiner—Cary O'Connor
Assistant Examiner—Ryan Carter
Attorney, Agent, or Firm—Robert H. Barrigar

[57] ABSTRACT

A family of reusable hot/cold therapeutic compress appliances for application to a large number of different treated areas on the body of a patient, each member of the family being dimensioned to receive an integral number of standardly sized and dimensioned pouches containing a heat absorbing material. Individual compress appliances of the family comprise at least one sealed pouch containing a heat absorbing material contained within a sleeve comprising a relatively heat-conductive patient-contact surface, an adjacent outer adherent surface, and an insulant disposed between the sealed pouch and the outer adherent layer to reduce heat transfer occurring away from the patient-contact surface. Attachment means associated with the sleeve are co-operatively configured so as to releasably adhere to any location on the outer adherent surface, allowing the patient using the compress appliance to select a location of adherence that may provide a safe and therapeutic compressive loading.

21 Claims, 10 Drawing Sheets

REUSABLE HOT/COLD THERAPEUTIC COMPRESS APPLIANCE

This application claims the benefit of U.S. Provisional application Ser. No. 60/013,935, filed Mar. 22, 1996.

FIELD OF THE INVENTION

This invention relates in general to therapeutic devices, and more particularly to appliances suitable for hot and cold compress therapy.

BACKGROUND OF THE INVENTION

Hot and cold compress therapy is an increasingly recognized medical technique for the successful treatment of many injuries. In general, hot compress therapy is used in cases of chronic ailments to relieve pain, increase blood flow, decrease joint stiffness, relieve muscle spasms and cramps, and increase the extensibility of scar tissue. Cold compress therapy is typically applied within approximately 72 hours following trauma or injury (such as laceration, sprains, strains, insect bits, and minor burns) to decrease blood flow, thereby helping to reduce localized pain and swelling. By containing the severity of swelling, cold compress therapy can have a significant impact on the healing process and speed of recovery.

An important factor influencing the therapeutic value of an appliance used for hot and cold compress therapy is its ability to maintain a hot or cold temperature, with minimal temperature fluctuation, for a therapeutically significant period of time—typically about 20 to 30 minutes. Another important factor influencing the therapeutic value of an appliance used for hot and cold compress therapy is its ability to provide a safe and tolerably comfortable level of compression. Other important and advantageous characteristics of appliances used for hot and cold compress therapy include convenience of use (which may be enhanced by providing a custom "hands-off" fit so that the appliance may be worn while the patient remains mobile, and by providing an appliance that may be used on several different areas of the body), and the ability to create a family of hot and cold compress appliances for application to many parts of the body while utilizing a minimum number of differently configured packages of heating or cooling material.

Although hot and cold compress appliances in general are known, none of the prior-known compress appliances adequately meet the foregoing therapeutic and practical objectives.

SUMMARY OF THE INVENTION

Described herein is a family of appliances intended for hot and cold compress therapy, the individual members of which encompass some or all of the following set of characteristics forming a partial list of features improving or enhancing the therapeutic and commercial value of appliances intended for use in hot and cold compress therapy:

a) selected composition of the heating and cooling material such that it maintains a relatively constant temperature for a therapeutically significant period of time;

b) vacuum-packing of the heating and cooling material;

c) composition and insulative properties of materials surrounding the heating and cooling material such that excessive heat is not lost to nor absorbed from the ambient surroundings;

d) provision of a safe and tolerably comfortable level of compression through choice of materials used to construct the appliance and/or through provision of elastic straps of suitable length and tensile strength;

e) the ability to repeatedly heat and cool the entire appliance without deterioration of the appliance of the heating and cooling material;

f) convenience of use through the provision of means to achieve a custom fit; and, g) the ability to create a family of useful appliances using only a limited number of different sizes of heating and cooling material packages.

It will be understood that, for any given appliance of the family intended for hot and cold compress therapy, as many of these characteristics as are consistent with function of the particular appliance may be included, so as to maximize the therapeutic and commercial advantage of that appliance. However, it will be further understood that one or several of these characteristics may be selectively omitted from any given appliance of the family for ease of manufacture, economic or other reasons.

Factors that affect the heat transfer characteristics of an appliance used for hot and cold compress therapy may include: (a) composition of the heating or cooling material—preferably a gel; (b) the presence or absence of air in and around the heating and cooling material; and (c) the presence or absence of insulating materials surrounding the heating or cooling material on one or more sides and, if present, their structure and composition. Preferably, the temperature fluctuation of the heat (or cold) applied to a treated area by an appliance used for hot and cold compress therapy should not exceed about 1° Celsius over a therapeutically significant period of time. The ability of a hot and cold compress appliance to provide a safe and tolerably comfortable level of compression may be facilitated through the choice of materials used to construct the appliance, as well as through the provision of elastic straps of suitable length and tensile strength to be used to hold the appliance to the injured body part.

It is possible to devise a relatively large family of useful appliances suitable for application to a large number of body parts for adults and at least larger children with the use of a single size and configuration of hot/cold pouch (containing the heating or cooling material) removably insertable into a suitably designed sleeve, as will be hereinafter described. A larger family of appliances in accordance with the invention may be provided by using, in addition to the sealed pouch size aforesaid, a somewhat larger pouch suitable for use with larger body areas to be treated, or with appliances whose shape necessitates the use of a larger size pouch than the minimum size. For a yet larger family of appliances, one or more larger or smaller sizes of pouch and sleeve may be used, but three different sizes have been found to be sufficient to treat most injuries. Further, some appliances may be designed to incorporate two or more sleeves, at least one of which is dimensioned to receive the large of two pouches, and at least one other of which is dimensioned to receive the smaller of two pouches.

Desirably, each pouch is vacuum-sealed and any printed matter thereon appears on a layer of plastic within the pouch that is visible through one or more overlying layers of transparent or near-transparent plastic. The outer layers of the pouch should be made of materials chosen to be non-allergenic and non-toxic. As pigments used in printing are sometimes allergenic or toxic, they should be disposed within or under overlying materials that themselves are neither toxic nor allergenic. Equally, other materials used in the construction of the sleeves and strapping to be described should be chosen to be non-allergenic and non-toxic.

Another important characteristics of all materials selected for use in appliances according to the invention is that they be readily heatable in a microwave oven, and readily coolable in a household freezer without damage so that repeated freezing or heating may be possible without serious deterioration over a relatively large number of uses of the appliance.

The sleeve in which the pouch is inserted should be designed to have a patient-contact surface selected to transfer heat readily as between the patient and the pouch without causing the skin of the patient to reach an uncomfortably extreme temperature. A woven nylon layer has been found suitable for such purpose; other materials of course could be chosen consistent with the foregoing criteria. The pouch within the sleeve makes immediate contact with this patient-contact surface of the sleeve, which in turn, as mentioned, makes direct contact with the treated area of the body of the patient. Preferably, that portion of the sleeve in contact with the opposed surface of the pouch not making contact with the patient-contact surface is relatively well insulated, as by the insertion of an insulating foam layer or the like interposed between the pouch and the outer surface of the sleeve opposite the patient-contact surface. That outer surface of the sleeve is preferably selected to be of a material to which a Velcro® or other similar multi-hooked plastic fastener will readily adhere. This characteristic is important in order that the strapping to be used in association with the sleeve can be attached to virtually any portion of this outer surface layer of the sleeve.

Preferably, there is a sleeve opening at one end of the sleeve into which the pouch may be inserted, and is itself closeable by means of a Velcro® or equivalent fastener. In most cases the pouch and the overall configuration of the sleeve can be formed as a somewhat rounded flexible parallelepiped, whose shape and configuration can be adjusted to conform to the limb or body surface of the patient undergoing treatment. All materials used in the pouch and the sleeve should be selected to permit such flexibility. The overall shape and size of a smaller pouch (or the only pouch if only one pouch is used in the family of appliances) should be sufficient to cover most of the surface of a knee, elbow, hand or foot (and thus necessarily a wrist or ankle) thereby affording capability of therapeutic use of the most commonly injured body parts. However, for larger injured body parts, such as thighs and portions of the back or chest, a larger pouch and sleeve combination is preferred. The size is to a great extent arbitrary, but typically a size that wraps most of the way around the thigh and extends from just above the knee to just below the groin will be acceptable. Smaller sizes for children or smaller body portions needed treatment, or longer sizes for ease of wrapping around large body portions (e.g. the head) may be also used as required.

Of course, other pouch sizes may be used, and in some cases a particular sleeve may be configured to hold two or more pouches. For example, a pouch that would fit completely around the neck would typically have to be longer than the smallest sized pouch described above; accordingly it may be desirable to use two contiguous pouches aligned end to end within a single elongated sleeve suitable for wrapping around the neck or head, or else a single longer pouch, as mentioned.

Equally, it is possible within the scope of the invention to combine sleeves of different sizes and pouches of different sizes to accommodate injuries that involve a larger body surface area and a more or less contiguous smaller body area. For example, if the upper arm and the shoulder are injured, a larger size sleeve and pouch could be used on the shoulder, and a smaller sized sleeve and pouch could be used on the upper arm. The two sleeves could be joined to one another as by stitching in order to facilitate the use of the combined appliance.

In some cases, the appliance may not be intended to be strapped to the user. For example, the appliance could be in the form of a cushion or pillow against which the patient rests a portion of the body, such as the head. In such case, the appliance may preferably be designed as having an inner resilient foam core, a pouch surrounding the foam core, and one or more layers interposed between the pouch and the user. Depending upon the intended use of any such appliance, the pouch could occupy a greater or lesser peripheral portion of such appliance, and the outer layer of such appliance could be selected to be of greater or lesser heat-transfer characteristics than might be preferred for an appliance strapped to the patient.

For those appliances that are strapped to the patient, it is desirable that the manner of strapping not be impeded by any arbitrary constraints. Accordingly, fixed-position buckles and the like should be avoided. Furthermore, the length of strapping should be selected so that the patient is able to attach and release the appliance to the injured part of the body with minimum difficulty—this in turn implies that the area in which one end of the strap makes constraining contact with the sleeve or other end of the strap (or of another strap) should be readily adjustable to accommodate the ease of reach of the patient. This in turn suggests that optimal design would permit the patient to adhere the strap to virtually any portion of the upper surface area of the appliance. This objective strongly indicates a preference for Velcro®-type fasteners on the strapping so that the straps may be adhered to any selected portion of the Velcro®-compatible outer layer of the sleeve. Further, the lengths of strapping should be chosen such that when the strapping is wrapped around that portion of the body required to constrain the appliance next to the body, only a slight surplus of the strapping is available for adherence to the appliance. Obviously some excess of length of the strapping will exist when the appliance is mounted on a relatively small portion of the patient's body, such as a wrist, since the same appliance may also have to be used for other larger parts of the patient's body such as the knee. But if the strapping is readily positionable, and the point of adherence of the strap to the appliance is not confined to only a small number of attachment points on the appliance, then an adequate choice of strap-attachment position is ordinarily possible. If desired, the strapping itself may be provided with additional Velcro® fasteners or similar adhesion means so that a trailing end of the fastener could be looped and affixed to the strap itself instead of to the sleeve.

The strapping should be readily easily stretchable, and is preferably selected to be of a readily stretchable rubber or suitable elastomer. It should not be selected to be of a relatively stiff, non-stretchable material (such as neoprene, for example). The amount of tension in the strapping is readily adjustable by selecting the point of attachment of the free end of the strapping on the outer surface of the sleeve. Accordingly, it is readily possible for the patient to adjust the tension to suit the therapeutic objective and the patient's own comfort. It has been found that stretchability permitting up to about a 50% increase in length in fully-stretched condition relative to rest condition of the strapping is appropriate.

Although most materials are adequately flexible for use in appliances of the sort described when warm, there is a tendency of many materials to become relatively inflexible when cold. Consequently, special care has to been taken in accordance with the invention to select the materials for the heating/cooling material for use in cold compress situations. The heating/cooling material should not become unduly stiff or inflexible when used as such, bearing in mind that the temperature range in household freezers can vary considerably from one freezer to another. Preferably the heating/cooling material is a gel that maintains a flexible consistency even at the lower extreme of freezer temperatures. There is little consensus among health care professionals as to what degree of cold flexibility is necessary or helpful in a cold compress appliance, so in certain applications one may wish to use a gel including up to about 40% propylene glycol as an antifreezer, but I prefer that the gel material include up to about 30% of propylene glycol for this purpose, and that cellulosic material rather than starch be used as a dispersion medium. Further particulars of preferred heating/cooling material formulations appear later in this specification. Propylene glycol is particularly advantageous in that it inhibits bacterial growth and helps to retain moisture in the pouch, as well as having the previously mentioned desirable non-allergenic, non-toxic and water soluble characteristics.

For greater acceptance and use by children of one or more of the appliances described herein, it will be clear that animating appendages such sa ears and a tail could readily be added to such appliance(s). In addition, one or more of the appliances described herein may clearly have application, with or without alterations, to equestrian or other animal patients.

BRIEF DESCRIPTION OF THE DRAWINGS

A detailed description of preferred embodiments of the invention is provided herein below with reference to the following schematic illustrations, in which.

Figure 1:
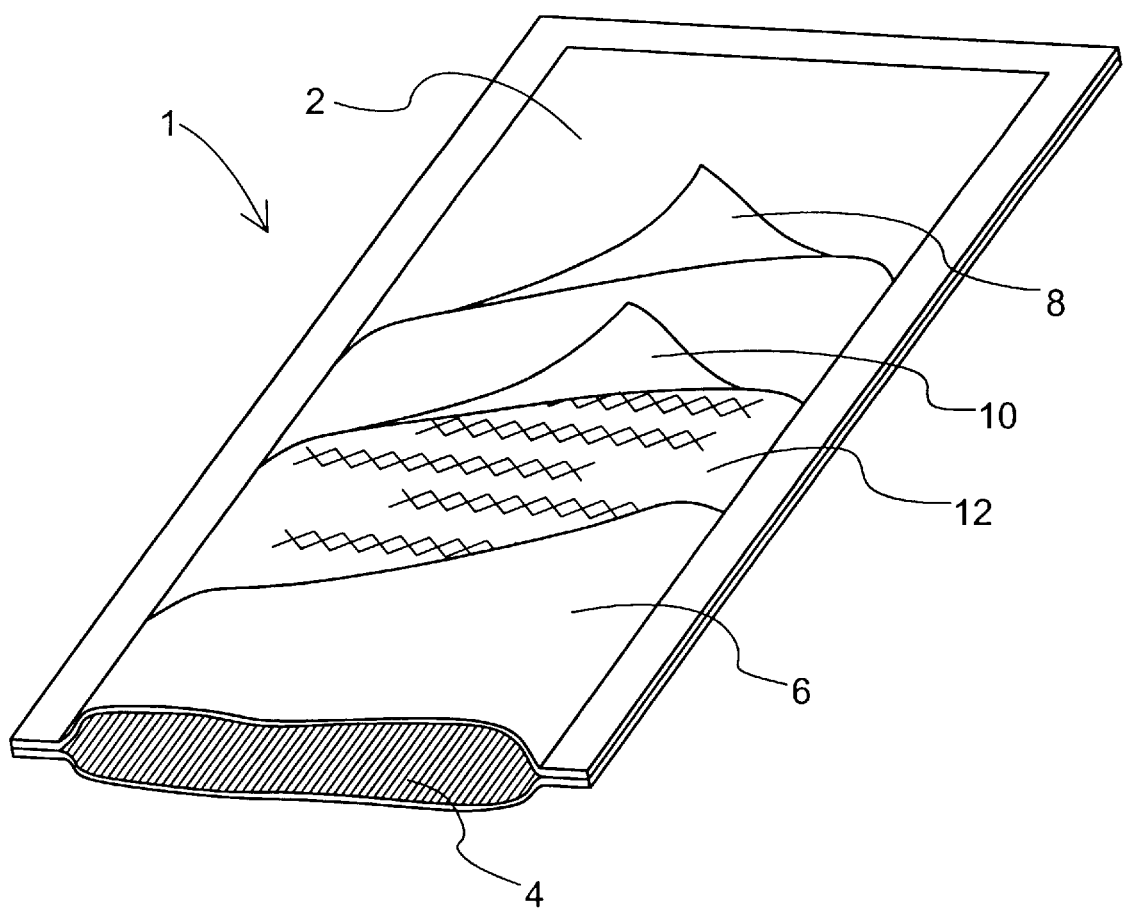
FIG. 1, in a partially sectional isometric view, illustrates a reusable sealed hot/cold pouch in accordance with a preferred embodiment of the present invention.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION

Referring to FIG. 1, there is illustrates in a partially sectional isometric view a reusable sealed hot/cold pouch in accordance with a preferred embodiment of the present invention. The pouch illustrated and generally designated 1 comprises strong flexible plastic material 2 containing pliable heat absorbing material 4, and is preferably microwaveable and able to endure both freezing and near-boiling temperatures.

Sealed pouch 1 is preferably vacuum-sealed and hypoallergenic, and is preferably constructed of inner layer 6 and substantially transparent outer layer 8, laminated together with adhesive layer 10. Inner layer 6 is preferably constructed of 3 mm linear density polyethylene, onto which may be set printing 12, and is coated with adhesive layer 10, preferably comprising Adcote® 533/522B. Adhesive layer 10 is in turn enveloped by outer layer 8, preferably constructed of 75 gauge Nylon.

In accordance with one preferred embodiment of the present invention, sealed pouch 1 has a length of about 10 inches and a width of about 5 inches. In accordance with another preferred embodiment of the present invention, sealed pouch 1 has a length of about 15 inches and a width of about 10 inches. In accordance with yet another preferred embodiment of the present invention, sealed pouch 1 has a length of about 24 inches and a width of about 3.5 inches.

Heat absorbing material 4 preferably has a relatively high specific heat capacity in order to maintain a given temperature for a lengthy period of time, remains pliable when subjected to freezing temperatures on the order of those that may be expected to be encountered in domestic or commercial freezers, is non-toxic, is bacteriostatic, is hydroscopic to avoid crystallization, and is sufficiently stable to withstand repeated heating and freezing. In accordance with a preferred embodiment of the present invention, heat absorbing material 4 comprises a gel substantially consisting of about 25% USP grade propylene glycol so as to maintain a gel freezing point of about −10° Celsius, about 22% Methocel® K15M hydroxypropyl methylcellulose as a colloidal dispersion medium, and about 53% filtered water. Preferably, heat absorbing material 4 does not contain any colouring, dyeing, or bittering agents. Gel constitutions of heat absorbing material 4 having about 20%–40% 1,2-propylene glycol or a like ratio of one or more homologs of 1,2-propylene glycol, and about 22% hydroxypropyl methylcellulose or a like ratio of other cellulose-based colloidal dispersion media, with the remaining ratio satisfied with filtered water are also contemplated.

Figure 2:
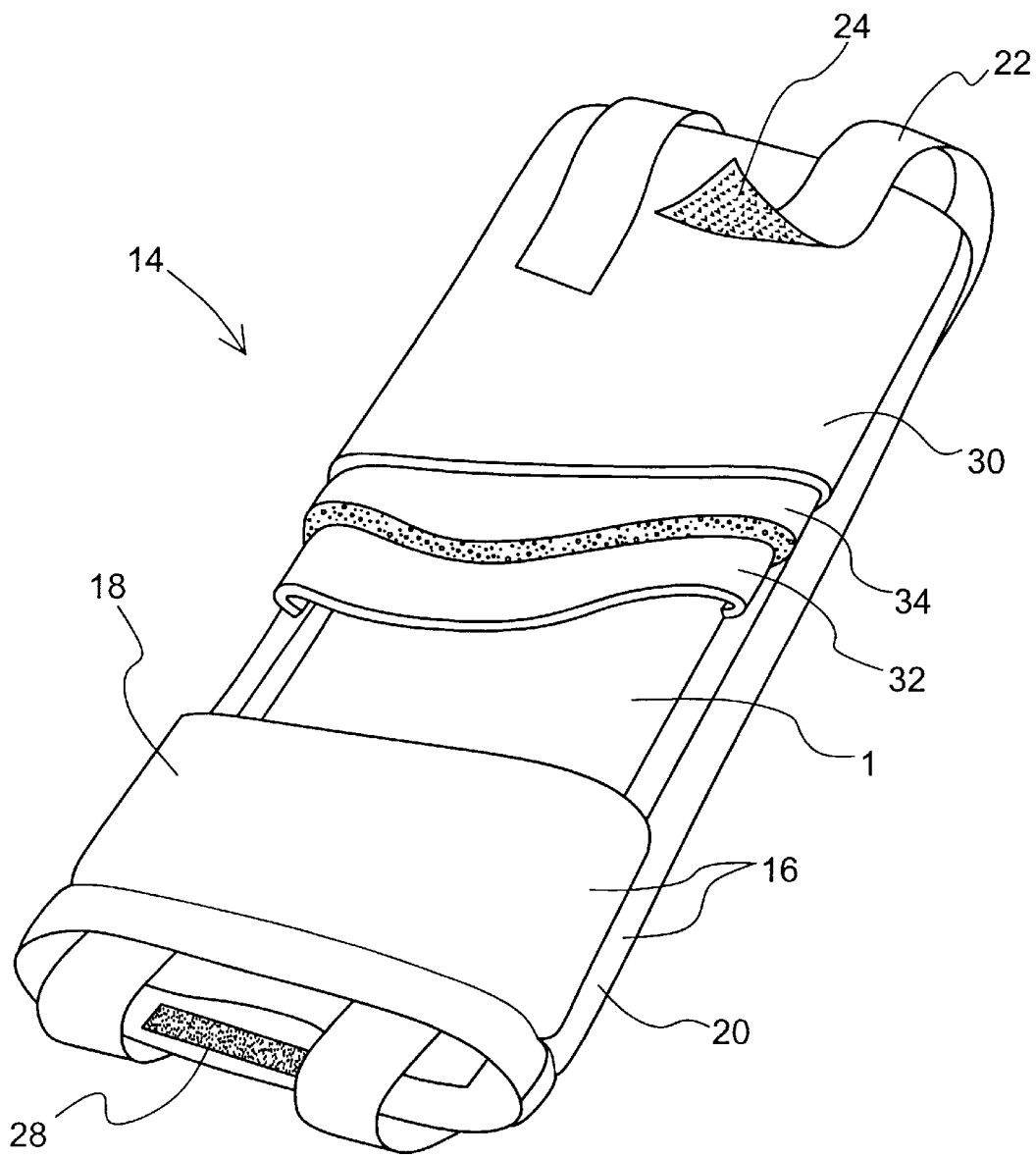
FIG. 2, in a partially sectional isometric view showing a hot/cold compress appliance in accordance with a preferred embodiment of the present invention, illustrates the structure of the outer shell of the sleeve portion of the appliance.
Figure 4:
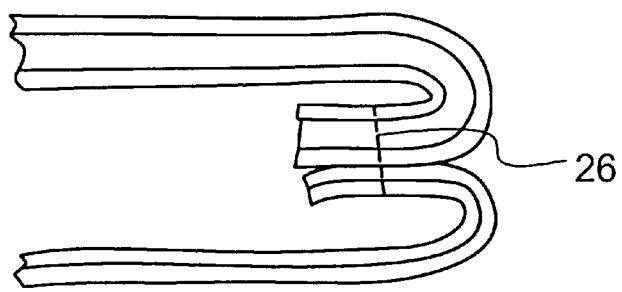
FIG. 4, in an enlarged fragmentary sectional view, illustrates the side seam of the sleeve portion of the hot/cold compress appliance of FIG. 2.
Figure 5:
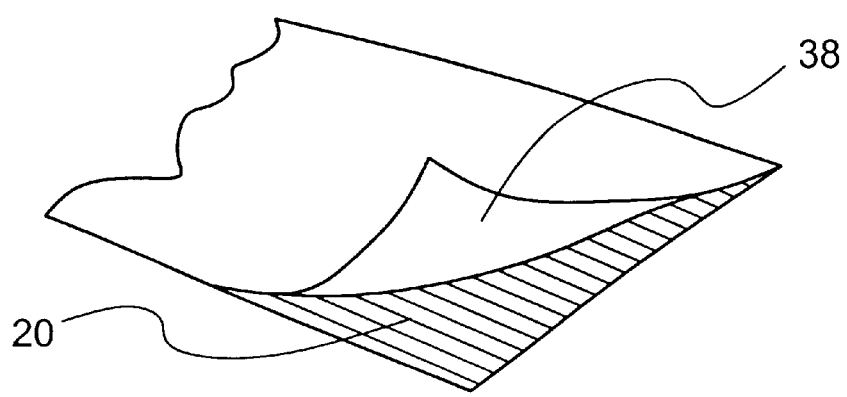
FIG. 5, in an enlarged fragmentary view, illustrates the structure of the patient-contact surface of the sleeve portion of the hot/cold compress appliance of FIG. 2.

Referring to FIG. 2, there is illustarted in a partially sectional isometric view a hot/cold compress appliance in accordance with a preferred embodiment of the present invention. The hot/cold compress appliance illustrated and generally designated 14 comprises sleeve 16 surrounding sealed pouch 1. Sleeve 16 generally comprises outer adherent surface 30, patient-contact surface 20, and insulant 34. In a preferred embodiment, outer adherent surface 30 and insulant 34 are combined in a single outer shell 18, and elastic strapping 22 with Velcro® fastening hook 24 is affixed to the distal end thereof. As is best seen in FIGS. 2 and 4, outer shell 18 of sleeve 16 is preferably joined permanently to patient-contact surface 20 of sleeve 16 on three sides by stitching 26 or by RF sealing, with the fourth side being re-sealably openable by engagement and disengagement of Velcro® fastening hook 28 with outer shell 18, in order to permit access to sealed pouch 1.

Outer shell 18 preferably comprises outer adherent surface 30, inner surface 32, and insulating core 34 between outer adherent surface 30 and inner surface 32 to limit heat transfer between sealed pouch 1 and the ambient surroundings through outer shell 18. Outer adherent surface 30 preferably engages Velcro® fastening hook 24 at any point along outer adherent surface 30 in order that hot/cold compress appliance 14 may be worn with a therapeutic level of compression around various areas of the patient's body, and in order that differences in size of individual user of hot/cold compress appliance 14 may be accommodated. In accordance with a preferred embodiment of the present invention, outer shell 18 of sleeve 16 comprises Veltex Bright® laminated loop fabric to enable the engagement of Velcro® fastening hook 24 at any point along outer adherent surface 30 of outer shell 18, inner surface 32 comprises nylon tricot backing, and insulating core 34 comprises polyester foam having a thickness of about 0.135 inches.

Patient-contact surface 20 is preferably hypoallergenic, and preferably increases user comfort by easing the shock of application to the body of a user of sealed pouch 1. In accordance with a preferred embodiment of the present invention, patient-contact surface 20 comprises 210 denier Nylon 36 coated on its inner surface with urethane 38 to prevent transfer to the user of condensation that may develop on the surface of sealed pouch 1.

Figure 3:
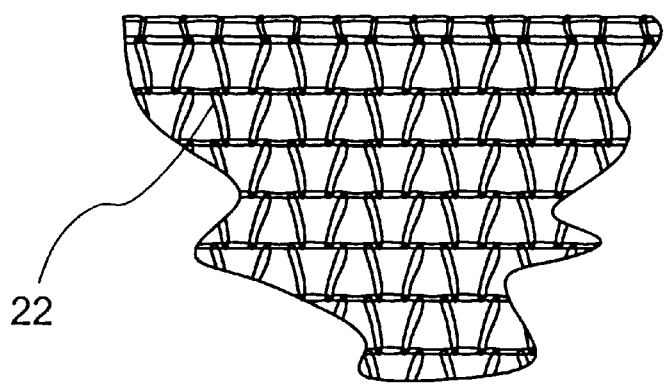
FIG. 3 is an enlarged fragmentary view of the elastic strapping of the hot/cold compress appliance of FIG. 2 that illustrates the fully-stretched structure of the elastic strapping.

Elastic strapping 22 is of a length suitable to attach hot/cold compress appliance 14 with a therapeutic level of compression to various areas of the body and to accommodate differences in size of individual users of hot/cold compress appliance 14, and is preferably microwave and laundry detergent safe. As best illustrated in FIGS. 2 and 3, in accordance with a preferred embodiment of the present invention, elastic strapping 22 comprise knit 1/150 polyester and 34-gauge extruded rubber, having a stretch of 140%.

As is best seen from FIGS. 6 through 20, for application to different parts of the body, hot/cold compress appliance 14 may be constructed to varying dimensions suited to accept one or more sealed pouches 1 having shape and size in accordance with the above-described preferred embodiments of sealed pouch 1 or other shapes and sizes as may be dictated by the anatomy desired to be treated. Preferably, a family of hot/cold compress appliances 14 created for application to all parts of the body will accept a minimum number of different shapes and sizes of sealed pouches 1, preferably having shape and size in accordance with the above-described preferred embodiments of sealed pouch 1. In a preferred embodiment of the present invention, a family of hot/cold compress appliances 14 for application to all parts of the anatomy that accepts one or more sealed pouches 1 having shape and size in accordance with the three above-described preferred embodiments of sealed pouch 1 is provided.

Figure 6:
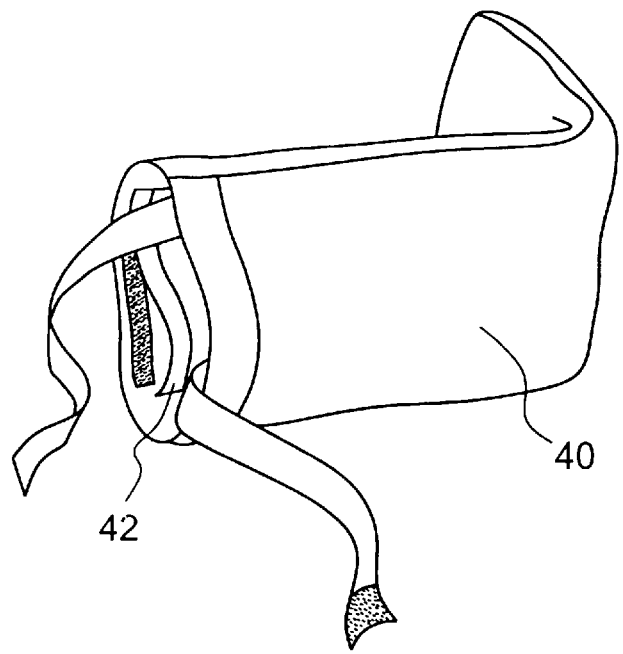
FIG. 6, in a perspective view, illustrates a small hot/cold compress appliance in accordance with a preferred embodiment of the present invention.
Figure 7:
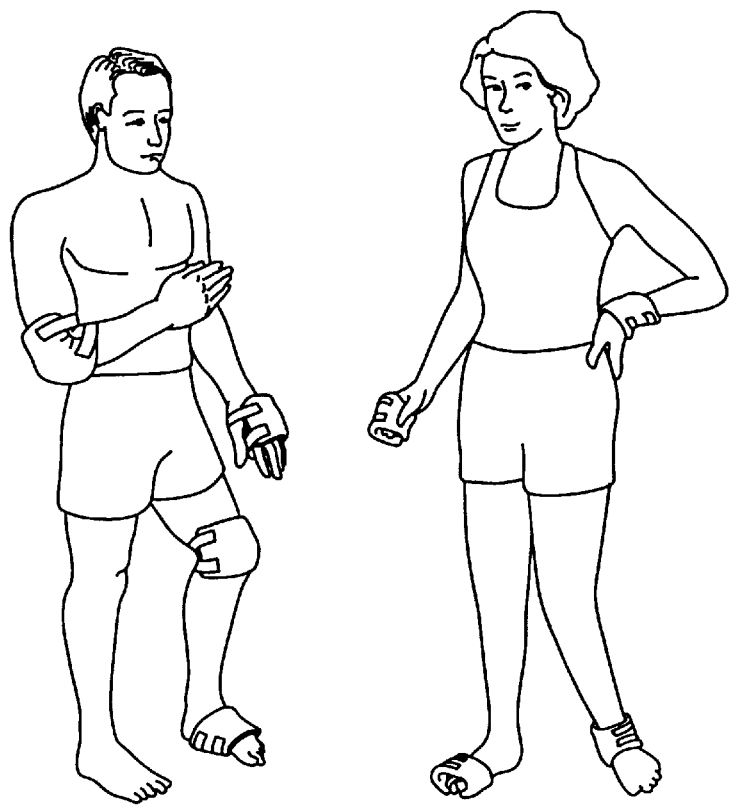
FIG. 7, in a front elevation view, illustrates the small hot/cold compress appliance of FIG. 6 as worn in representative positions on the body of a user.

Illustrated in FIGS. 6 and 7 in perspective view and in front elevation view respectively is small hot/cold compress appliance 40, preferably containing sealed hot/cold compress pouch 42 having a length of about 10 inches and a width of about 5 inches, for application to the elbow, wrist, hand, fingers, knee, foot, ankle, and toes.

Figure 8:
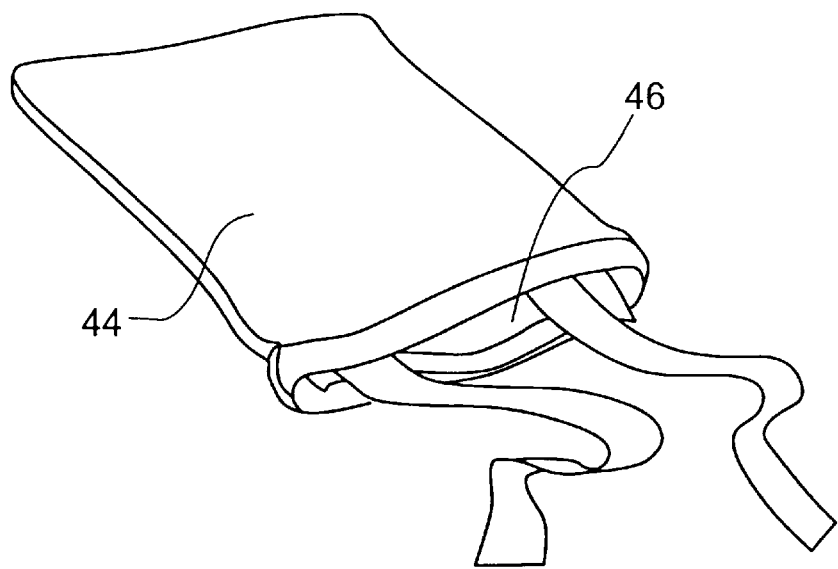
FIG. 8, in an isometric view, illustrates a large hot/cold compress appliance in accordance with a preferred embodiment of the present invention.
Figure 9:
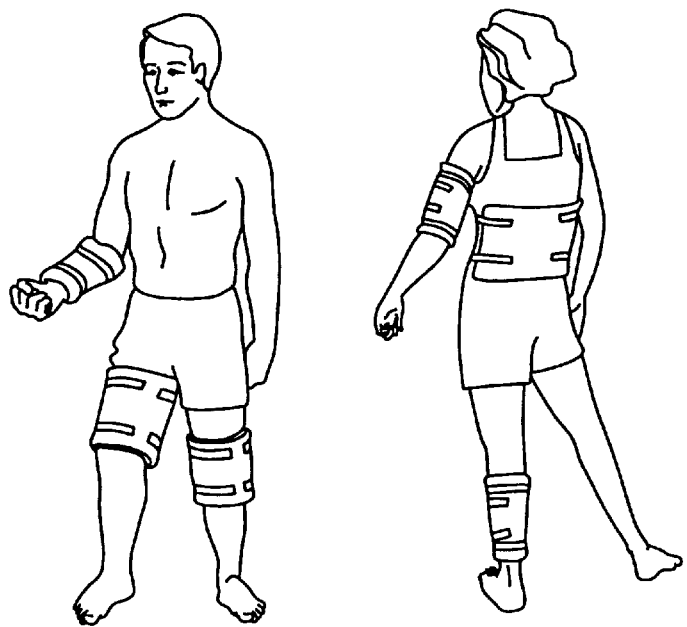
FIG. 9, in an elevation view, illustrates the large hot/cold compress appliance of FIG. 8 as worn in representative positions on the body of a user.

Illustrated in FIGS. 8 and 9 in isometric view and in elevation view respectively is large hot/cold compress appliance 44, preferably containing sealed hot/cold compress pouch 46 having a length of about 15 inches and a width of about 10 inches, for application to the thigh, hamstring, knee, torso, arm, shin, and calf.

Figure 10:
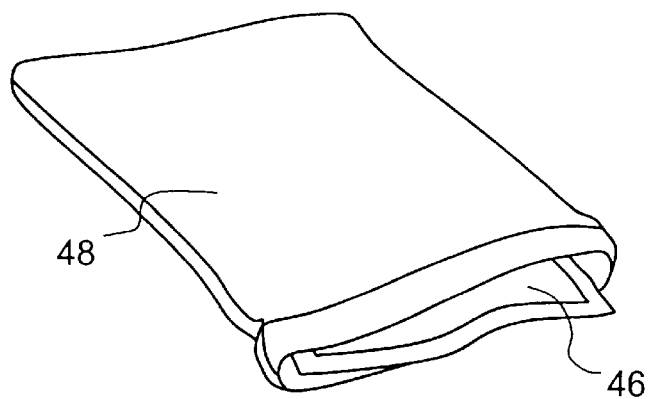
FIG. 10, in an isometric view, illustrates a hot/cold compress appliance in accordance with a preferred embodiment of the present invention.
Figure 11:
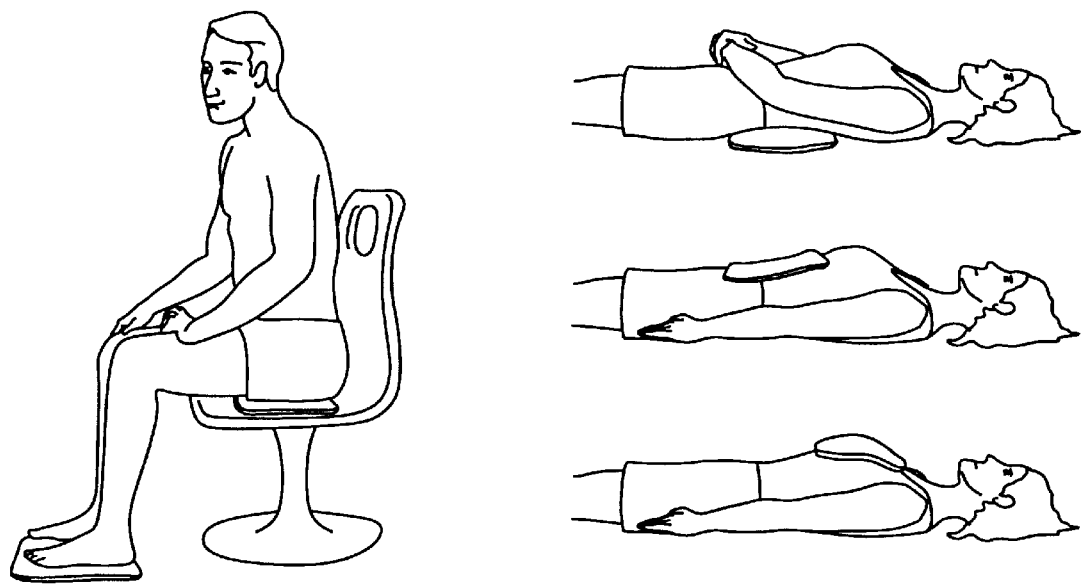
FIG. 11, in a side elevation view, illustrates the hot/cold compress appliance of FIG. 10 as applied to representative portions of the body of a user.

Illustrated in FIGS. 10 and 11 in isometric view and in side elevation view respectively is seat-back hot/cold compress appliance 48, preferably containing sealed hot/cold compress pouch 46 having a length of about 15 inches and a width of about 10 inches, for application to the abdomen, seat, chest, and feet.

Figure 12:
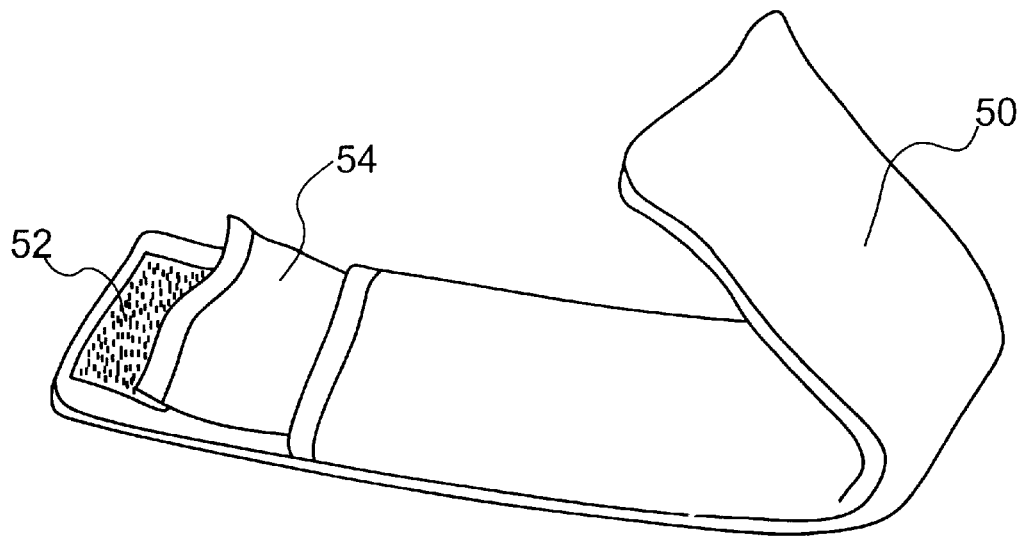
FIG. 12, in a perspective view, illustrates a hot/cold compress appliance in accordance with a preferred embodiment of the present invention.
Figure 13:
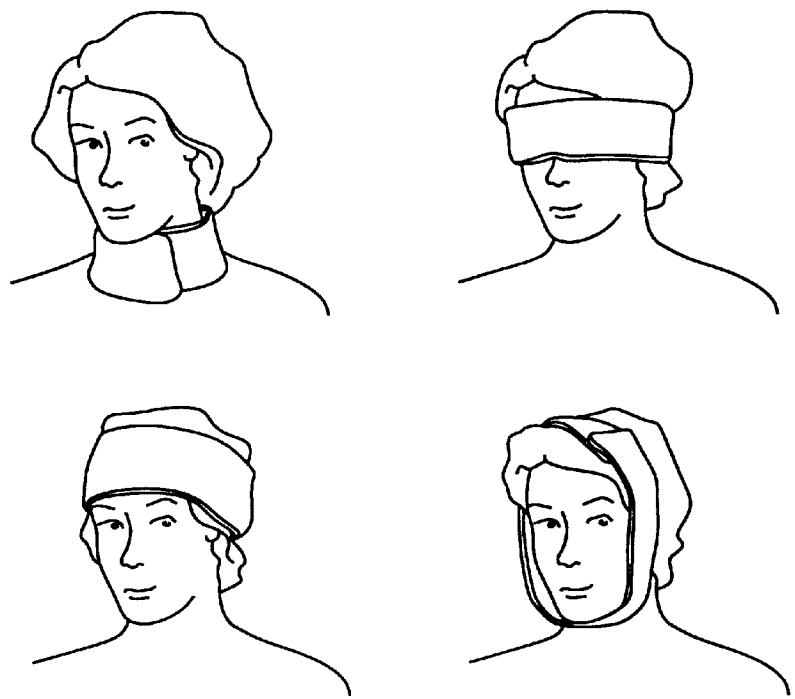
FIG. 13, in a front elevation view, illustrates the hot/cold compress appliance of FIG. 12 as worn in representative positions on the head and neck of a user.

Illustrated in FIGS. 12 and 13 in perspective view and in front elevation view respectively is head-neck hot/cold compress appliance 50, having Velcro® fastening hook 52 and preferably containing sealed hot/cold compress pouch 54 having a length of about 24 inches and a width of about 3.5 inches, for application to the head and neck.

Figure 14:
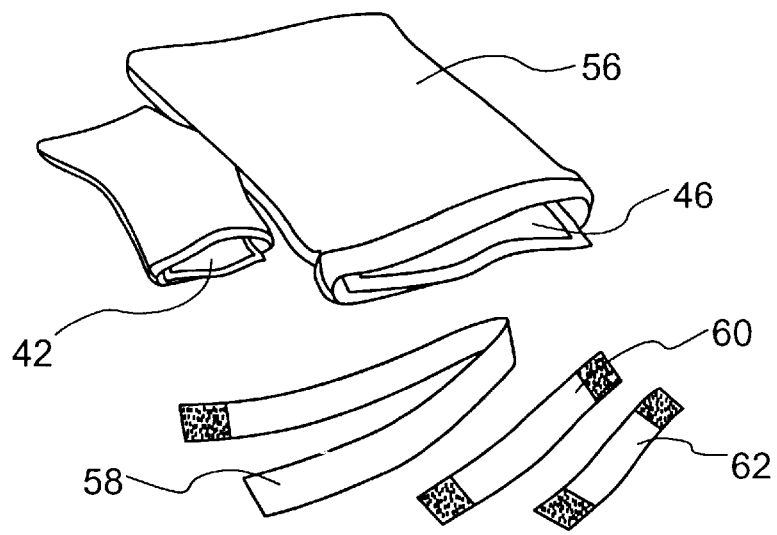
FIG. 14, in a partially exploded perspective view, illustrates a hot/cold compress appliance in accordance with a preferred embodiment of the present invention.
Figure 15:
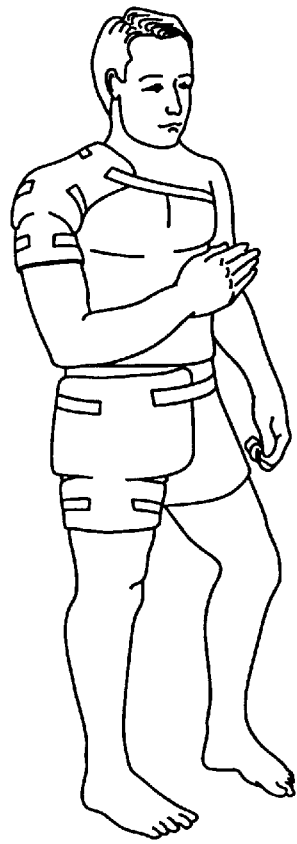
FIG. 15, in a front elevation view, illustrates the hot/cold compress appliance of FIG. 14 as worn in representative positions on the body of a user.

Illustrated in FIGS. 14 and 15 in partially exploded perspective view and in front elevation view respectively is shoulder-hip hot/cold compress appliance 56, preferably containing sealed hot/cod compress pouch 42, having a length of about 10 inches and a width of about 5 inches, and sealed hot/cold compress pouch 46 having a length of about 15 inches and a width of about 10 inches, for application to the shoulder/upper arm and hip/upper thigh. Elastic strapping 58, 60, and 62 is preferably completely detachable form shoulder-hip hot/cold compress appliance 56 to accommodate diverse placement of elastic strapping 58, 60, and 62 on appliance 56 during use.

Figure 16:
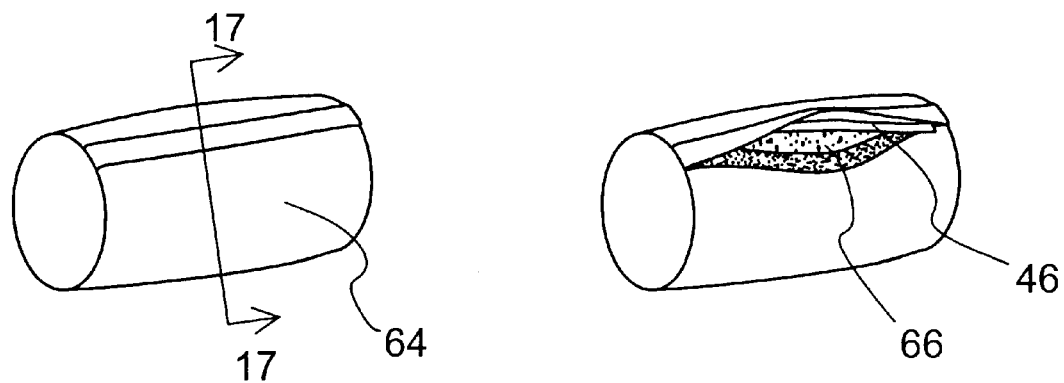
FIG. 16, in an isometric view, illustrates a hot/cold compress appliance in accordance with a preferred embodiment of the present invention.
Figure 17:
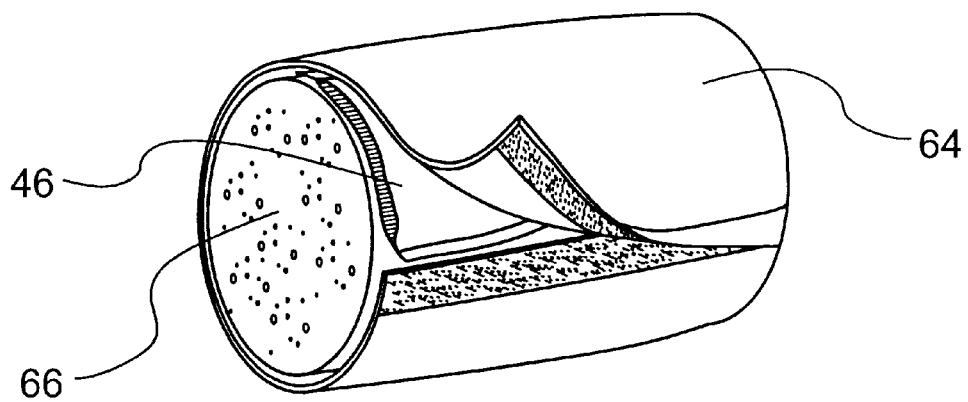
FIG. 17, in a cross-sectional view taken along line 17—17 in FIG. 16, illustrates the internal structure of the hot/cold compress appliance of FIG. 16.
Figure 18:
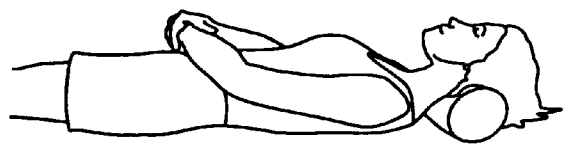
FIG. 18, in a side elevation view, illustrates the hot/cold compress appliance of FIG. 16 as applied to the body of a user.

Illustrated in FIGS. 16, 17, and 18 in isometric view, cross-sectional view taken along line 17—17 in FIG. 16, and side elevation view respectively is cervical pillow hot/cold compress appliance 64, preferably containing hot/cold compress pouch 46 having a length of about 15 inches and a width of about 10 inches, for application to the back of the neck for treatment of neck and back pain, headache, fever, muscle spasm, or cramps. Cervical pillow hot/cold compress appliance 64 is preferably about 15 inches in length and about 5.5 inches in diameter, and contains, in addition to hot/cold compress pouch 46, polyurethane foam core 66 having an Indentation Load Deflection of about 141 lbs (1.1 lbs. per square foot). Cervical pillow hot/cold compress appliance 64 preferably conserves heat or cold for a minimum of four hours.

Figure 19:
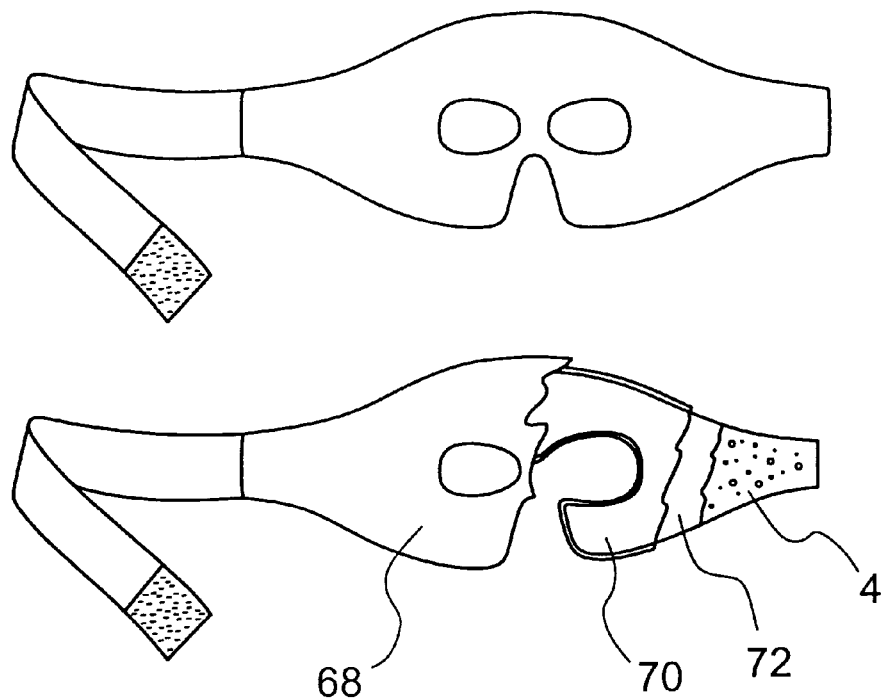
FIG. 19, in a partially sectional isometric view showing a hot/cold compress appliance in accordance with a preferred embodiment of the present invention, illustrates the structure of the appliance; and, FIG. 20, in a front elevational view, illustrates the hot/cold compress appliance of FIG. 19 as worn on the face of a user.
Figure 20:
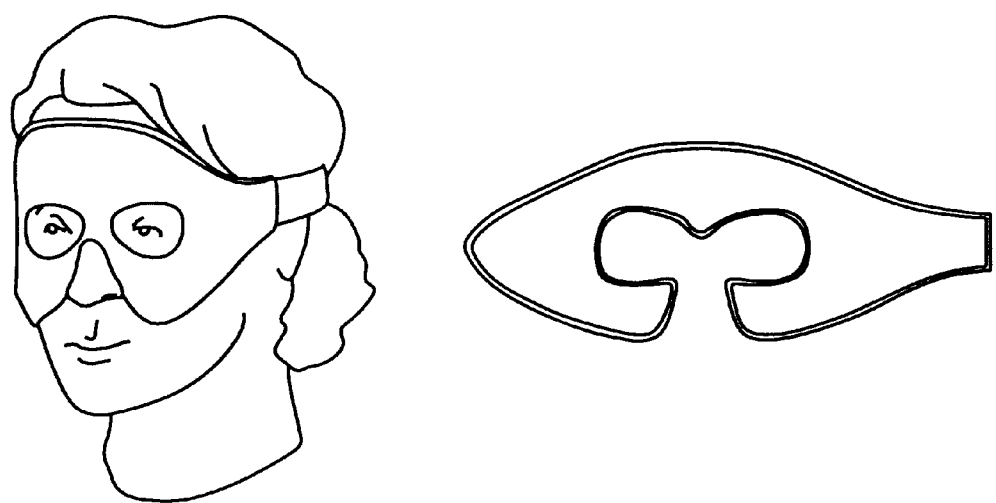

Illustrated in FIGS. 19 and 20, in partially sectional isometric view and front elevation view respectively, is face pad hot/cold compress appliance 68, preferably containing hot/cold compress pouch 70 permanently affixed therein. Hot/cold compress pouch 70 preferably comprises ultrasonically RF sealed 10-gauge frosted vinyl pouch 72 containing gel 4.

I claim:

1. A reusable hot/cold therapeutic compress appliance for one of heating and cooling a treated area of the body of a patient, said reusable hot/cold therapeutic compress appliance comprising:
   a) a sealed pouch comprising a strong flexible plastic material and containing a pliable heat absorbing material, the mass, dimensions, and specific heat capacity of said sealed pouch containing said pliable heat absorbing material being selected such that at standard temperature and pressure (STP) said sealed pouch containing said heat absorbing material will maintain a temperature (over the range from about 0° Celsius to about 60° Celsius) within at least about 10° Celsius for a time of at least about 20 minutes;
   b) a sleeve for containing said sealed pouch, said sleeve comprising:
      i) a relatively heat-conductive patient-contact surface for placement over the treated area selected to facilitate the maintenance of a relatively constant temperature gradient across said patient-contact surface,
      ii) an outer adherent surface adjacent the patient-contact surface,
      iii) and an insulant disposed between said outer adherent surface and said sealed pouch (contained within said sleeve) in order to reduce heat transfer between said sealed pouch and said outer adherent surface; and,
   c) attachment means associated with said sleeve, said attachment means being co-operatively configured so as to releasably adhere to any location on said outer adherent surface, whereby the patient using said compress appliance may select a location of adherence so as to provide a comfortable and therapeutic compressive loading to the treated area.

2. The reusable hot/cold therapeutic compress appliance of claim 1 wherein said attachment means comprise at least one elongate elastic strap having a fixed end affixed to said sleeve and a free end, said at least one elastic strap being co-operatively configured proximate to said free end so as to releasably adhere to any location on said outer adherent surface, said at least one elastic strap further being of a length and tensile strength such that a comfortable and therapeutic compressive loading of the treated area may be achieved with the compress appliance when the compress appliance is placed over the treated area and said free end of said at least one elastic strap is attached to said outer adherent surface at a location of adherence selected by the patient.

3. The reusable hot/cold therapeutic compress appliance of claim 1 in which said attachment means comprise at least one elongate detachably attachable elastic strap being co-operatively configured proximate to both ends so as to releasably adhere to any location on said outer adherent surface, said at least one detachably attachable elastic strap further being of a length and tensile strength such that a comfortable and therapeutic compressive loading of the treated area may be achieved when said compress appliance is placed over the treated area and said both ends of said at least one detachably attachable elastic strap are attached to said outer adherent surface at locations of adherence selected by the patient.

4. The reusable hot/cold therapeutic compress appliance of claim 1 wherein said pliable heat absorbing material is vacuum-packed within said sealed pouch in order that heat transfer between said pliable heat absorbing material and said sealed pouch may be substantially uniform at all points along said sealed pouch.

5. The reusable hot/cold therapeutic compress appliance of claim 1 wherein said pliable heat absorbing material comprises a gel substantially consisting of about 20–30% 1,2-propylene glycol and about 22% of a cellulose-based colloidal dispersion media, with the remaining ratio satisfied with water, so that said gel remains pliable when subjected to temperatures on the order of those that may be expected to be encountered in domestic and commercial freezers.

6. The reusable hot/cold therapeutic compress appliance of claim 5 wherein said pliable heat absorbing material comprises a gel substantially consisting of about 25% USP grade 1,2-propylene glycol and about 22% hydroxypropyl methylcellulose, with the remaining ratio satisfied with filtered water, in order that said gel may have a freezing point of about −10° Celsius.

7. The reusable hot/cold therapeutic compress appliance of claim 1 wherein said sealed pouch is removably contained within said sleeve.

8. The reusable hot/cold therapeutic compress appliance of claim 1 wherein said outer adherent surface and said insulant are combined in a single outer shell.

9. The reusable hot/cold therapeutic compress appliance of claim 8 wherein said insulant within said outer shell comprises polyester foam in order that said outer shell be capable of withstanding without damage such freezing temperatures as may be expected to be encountered in domestic or commercial freezers, as well as being capable of withstanding heating in a microwave oven without damage.

10. The reusable hot/cold therapeutic compress appliance of claim 1 in which said patient-contact surface comprises a nylon material so that said patient-contact surface may be substantially hypo-allergenic.

11. The reusable hot/cold therapeutic compress appliance of claim 10 wherein said nylon material is associated with a relatively moisture-impermeable substance in order to impede the passage of moisture through said patient-contact surface.

12. The reusable hot/cold therapeutic compress appliance of claim 1 wherein said plastic material of said sealed pouch comprises an inner plastic layer upon which printing may be set, and an outer substantially transparent plastic layer affixed to said inner plastic layer with an adhesive, in order that potentially allergenic or toxic pigments used to form said printing do not come into contact with the patient using said compress alliance.

13. The reusable hot/cold therapeutic compress appliance of claim 2 wherein said at least one elastic strap has a maximal stretch of about 140%.

14. The reusable hot/cold therapeutic compress appliance of claim 3 wherein said at least one detachably attachable elastic strap has a maximal stretch of about 140%.

15. The reusable hot/cold therapeutic compress appliance of claim 2 wherein said at least one elastic strap comprises knit polyester and rubber in order that said at least one elastic strap may be capable of withstanding without damage such freezing temperatures as may be expected to be encountered in domestic or commercial freezers, as well as being capable of withstanding heating in a microwave oven without damage.

16. The reusable hot/cold therapeutic compress appliance of claim 3 wherein said at least one detachably attachable elastic strap comprises knit polyester and rubber in order that said at least one detachably attachable elastic strap may be capable of withstanding without damage such freezing temperatures as may be expected to be encountered in domestic or commercial freezers, as well as being capable of withstanding heating in a microwave oven without damage.

17. A family of reusable hot/cold therapeutic compress appliances for application to a large number of different treated areas on the body of a patient, each said compress appliance of said family comprising:
   a) at least one sealed pouch of a standard size and configuration, said at least one sealed pouch comprising a strong flexible plastic material and containing a pliable heat absorbing material, the mass, dimensions, and specific heat capacity of said sealed pouch containing said pliable heat absorbing material being selected such that at standard temperature and pressure (STP) said sealed pouch containing said heat absorbing material will maintain a temperature (over the range from about 0° Celsius to about 60° Celsius) within at least about 10° Celsius for a time of at least about 20 minutes; and,
   b) at least one sleeve for containing said at least one sealed pouch, said sleeve comprising:
      i) a relatively heat-conductive patient-contact surface for placement over the treated area,
      ii) an outer adherent surface adjacent the patient-contact surface,
      iii) and an insulant disposed between said outer adherent surface and said at least one sealed pouch (contained within said sleeve) in order to reduce heat transfer between said at least one sealed pouch and said outer adherent surface;

wherein said sleeves of all members of the family are dimensioned to receive an integral number of said at least one sealed pouch of a standard size and configuration.

18. The family of reusable hot/cold therapeutic compress appliances of claim 17 wherein two different sizes and configurations of said at least one sealed pouch are provided.

19. The family of reusable hot/cold therapeutic compress appliances of claim 18 wherein the dimensions of said at least one sealed pouch are one of about 10×5 inches and about 15×10 inches.

20. The family of reusable hot/cold therapeutic compress appliances of claim 17 wherein three different sizes and configurations of said at least one sealed pouch are provided.

21. The family of reusable hot/cold therapeutic compress appliances of claim 18 wherein the dimensions of said at least one sealed pouch are one of about 10×5 inches, about 15×10 inches, and about 24×3.5 inches.

* * * * *